United States Patent
Stevens et al.

(10) Patent No.: US 7,195,777 B2
(45) Date of Patent: Mar. 27, 2007

(54) METHOD AND APPARATUS FOR BLOWMODING CAPSULES OF POLYVINYLALCOHOL AND BLOWMOLDED POLYVINYLALCOHOL CAPSULES

(75) Inventors: Henry Guy Stevens, Malmesbury (GB); John Colin Dawson, Malmesbury (GB)

(73) Assignee: PVAXX Research & Development Limited, Gloucestershire (GB)

( * ) Notice: Subject to any disclaimer, the term of this patent is extended or adjusted under 35 U.S.C. 154(b) by 626 days.

(21) Appl. No.: 10/220,491

(22) PCT Filed: Mar. 1, 2001

(86) PCT No.: PCT/GB01/00931

§ 371 (c)(1),
(2), (4) Date: Dec. 13, 2002

(87) PCT Pub. No.: WO01/64421

PCT Pub. Date: Sep. 7, 2001

(65) Prior Publication Data

US 2003/0152619 A1    Aug. 14, 2003

(30) Foreign Application Priority Data

Mar. 1, 2000    (GB) ................................ 0005016.1

(51) Int. Cl.
*A61K 9/48*    (2006.01)
(52) U.S. Cl. ........................................ 424/451; 424/452
(58) Field of Classification Search .................. 424/451
See application file for complete search history.

(56) References Cited

U.S. PATENT DOCUMENTS

| | | | |
|---|---|---|---|
| 2,897,854 A | 8/1959 | Moreland | |
| 3,159,545 A | 12/1964 | Kidwell et al. | |
| 3,233,022 A | 2/1966 | Henry et al. | |
| 3,470,122 A | 9/1969 | Ridgeway et al. | |
| 3,713,965 A | 1/1973 | Widiger et al. | |
| 3,755,190 A * | 8/1973 | Hart et al. ............. | 427/213.34 |
| 3,791,802 A | 2/1974 | Holowaty | |
| 3,810,468 A | 5/1974 | Harper et al. | |
| 3,954,721 A | 5/1976 | Gross | |
| 3,980,663 A | 9/1976 | Gross | |
| 3,983,095 A | 9/1976 | Bashaw et al. | |
| 3,984,494 A * | 10/1976 | Harreus et al. ............... | 525/61 |
| 3,989,586 A | 11/1976 | Bashaw et al. | |
| 3,997,489 A | 12/1976 | Coker | |

(Continued)

FOREIGN PATENT DOCUMENTS

CA    890 833    1/1972

(Continued)

OTHER PUBLICATIONS

Kroschwitz, Concise Encyclopedia of Polymer Science and Engineering, 1990, John Wiley & Sons, USA.

*Primary Examiner*—S. Tran
(74) *Attorney, Agent, or Firm*—William E. Jackson; Stites & Harbison PLLC

(57) ABSTRACT

A capsule is formed from a PVA composition by blow moulding. Such capsules can at last provide a viable alternative to gelatin for bio-degradeable capsule containing a pharmaceutical or consumable or other substance, for example a detergent. The capsules may contain solid or liquid substances. Blow moulding apparatus suitable for forming such capsules is also disclosed and claimed.

10 Claims, 4 Drawing Sheets

U.S. PATENT DOCUMENTS

| | | | |
|---|---|---|---|
| 4,155,957 A | 5/1979 | Sasayama | |
| 4,194,901 A | 3/1980 | Gambacorta | |
| 4,206,101 A | 6/1980 | Wysong | |
| 4,248,819 A | 2/1981 | Mayer et al. | |
| 4,263,251 A | 4/1981 | Voegle | |
| 4,298,858 A | 11/1981 | Romanski | |
| 4,332,917 A | 6/1982 | Heslinga et al. | |
| 4,338,417 A | 7/1982 | Heslinga et al. | |
| 4,362,559 A | 12/1982 | Perez et al. | |
| 4,389,506 A | 6/1983 | Hassall, Jr. | |
| 4,409,171 A | 10/1983 | Leon et al. | |
| 4,418,163 A | 11/1983 | Murakami et al. | |
| 4,420,588 A | 12/1983 | Yoshioka et al. | |
| 4,424,016 A | 1/1984 | Matsuda et al. | |
| 4,436,682 A | 3/1984 | Knopp | |
| 4,469,837 A | 9/1984 | Cattaneo | |
| 4,616,063 A | 10/1986 | Le-Khac | |
| 4,666,983 A | 5/1987 | Tsubakimoto et al. | |
| 4,705,773 A | 11/1987 | Le-Khac | |
| 4,731,067 A | 3/1988 | Le-Khac | |
| 4,743,244 A | 5/1988 | Le-Khac | |
| 4,788,237 A | 11/1988 | Le-Khac | |
| 4,798,861 A | 1/1989 | Johnson et al. | |
| 4,813,945 A | 3/1989 | Le-Khac | |
| 4,849,256 A | 7/1989 | Newman et al. | |
| 4,880,868 A | 11/1989 | Le-Khac | |
| 4,892,533 A | 1/1990 | Le-Khac | |
| 5,176,751 A | 1/1993 | Findley | |
| 5,209,978 A * | 5/1993 | Kosaka et al. | 428/402.2 |
| 5,373,054 A | 12/1994 | Sanuki et al. | |
| 5,395,880 A | 3/1995 | Sato et al. | |
| 5,617,710 A * | 4/1997 | Goossens et al. | 53/471 |
| 5,656,682 A * | 8/1997 | Rimsa et al. | 524/37 |
| 5,811,488 A | 9/1998 | Narumoto et al. | |
| 5,814,266 A | 9/1998 | Pienkowski et al. | |
| 5,827,917 A | 10/1998 | Fourty | |
| 5,922,808 A | 7/1999 | Hanada et al. | |
| 5,948,848 A | 9/1999 | Giltsoff | |
| 6,054,519 A | 4/2000 | Jakob et al. | |
| 6,770,293 B2 * | 8/2004 | Angel et al. | 424/451 |
| 6,967,026 B2 * | 11/2005 | Hoshi et al. | 424/408 |
| 2001/0043999 A1 * | 11/2001 | Scott et al. | 428/36.6 |

FOREIGN PATENT DOCUMENTS

| | | |
|---|---|---|
| EP | 0 095 874 A1 | 12/1983 |
| EP | 0 101 253 A2 | 2/1984 |
| EP | 0 169 382 A2 | 1/1986 |
| EP | 0 213 799 A1 | 3/1987 |
| EP | 0 227 305 A2 | 7/1987 |
| EP | 0 232 121 A2 | 8/1987 |
| EP | 0 233 014 A2 | 8/1987 |
| EP | 0 264 208 A2 | 4/1988 |
| EP | 0 268 498 A2 | 5/1988 |
| EP | 0 269 393 A2 | 6/1988 |
| EP | 0 272 074 A2 | 6/1988 |
| EP | 0 326 382 A2 | 8/1989 |
| EP | 0 342 919 A2 | 11/1989 |
| EP | 0 397 410 A2 | 11/1990 |
| EP | 0 401 044 A2 | 12/1990 |
| EP | 0 404 723 A2 | 12/1990 |
| EP | 0 436 514 A2 | 7/1991 |
| EP | 0 635 545 A2 * | 1/1995 |
| GB | 0 937 057 A | 9/1963 |
| GB | 1 040 506 A | 8/1966 |
| GB | 1 272 617 A | 5/1972 |
| GB | 1 397 127 A | 6/1975 |
| GB | 2 022 505 A | 12/1979 |
| GB | 2 082 614 A | 3/1982 |
| GB | 2 126 591 A | 3/1984 |
| GB | 2 269 602 A | 2/1994 |
| GB | 2 270 030 A | 3/1994 |
| GB | 1 051 514 A | 12/1996 |
| IE | 97 280 | 9/1998 |
| JP | 01 022 500 | 1/1989 |
| JP | 04 081 440 | 3/1992 |
| JP | 06 179 235 | 6/1994 |
| JP | 10 250 701 | 9/1998 |
| JP | 2000289097 | 10/2000 |
| WO | WO 85/04365 A1 | 10/1985 |
| WO | WO 92/01556 A1 | 2/1992 |
| WO | WO 92/20329 A1 | 11/1992 |
| WO | WO 93/12275 A1 | 6/1993 |
| WO | WO 93/17066 A1 | 9/1993 |
| WO | WO 93/20141 A1 | 10/1993 |
| WO | WO 93/24684 A1 | 12/1993 |
| WO | WO 93/25735 A1 | 12/1993 |
| WO | WO 96/20973 A1 | 7/1996 |
| WO | WO 97/09379 A1 | 3/1997 |
| WO | WO 97/35537 A1 | 10/1997 |
| WO | WO 97/36722 A1 | 10/1997 |
| WO | WO 9735537 A1 * | 10/1997 |
| WO | WO 98/26911 A1 | 6/1998 |
| WO | WO 98/39382 A1 | 11/1998 |
| WO | WO 9929348 A1 * | 6/1999 |
| WO | WO 9946329 A1 * | 9/1999 |

* cited by examiner top of jaws

METHOD AND APPARATUS FOR BLOWMODING CAPSULES OF POLYVINYLALCOHOL AND BLOWMOLDED POLYVINYLALCOHOL CAPSULES

The present invention relates to capsules, particularly biodegradeable capsules and to apparatus and methods for forming such capsules.

There is a demand for biodegradable capsules. Such capsules can contain substances which, on biodegradation or solubilisation of the capsule walls, are released. Speed of release of the substance can be controlled, for example, by varying the thickness of the capsule wall. The demand for such capsules is particularly pronounced in relation to consumable capsules containing, for example, pharmaceutical substances or vitamin or mineral dietary supplements.

It is known to use gelatin to form such capsules for containing liquids. However, there is currently a significant and increasing demand for an alternative to or replacement for gelatin. This demand arises particularly in pharmaceutical applications from patients who are intolerant of gelatin. It is desirable to have an alternative source of material for forming such capsules. Another problem with gelatin capsules is that they are not generally suitable for containing dry or powdered substances.

A suitable substitute for a gelatin capsule not only must be biodegradable, in certain applications it must be edible and have an inoffensive taste, and it must of course be readily formable into capsules. The potential market for a suitable substitute for gelatin is major and various alternatives have been tried over many years but all suffer from various drawbacks. Also known are two-part capsules; these may impose different constraints on the material properties and are generally suitable only for containing powdered or dry substances. They are less suited to containing liquids and the two-part construction may lead to complications in forming and filling and/or may mean that the contents are not hermetically sealed.

The invention seeks in a general aim to provide a viable alternative to gelatin capsules.

In a first aspect, the invention comprises a capsule having walls formed, most preferably by blow moulding, from a PVA containing composition and containing a substance.

PVA has not hitherto been commercially manufactured into capsules containing a substance due to the well known and established conventional properties of PVA. However, the inventor has found that by making use of a PVA composition provided as a polymer feedstock in the form of a cold pressed compounded tablet or pellet, surprisingly reliable formation of such articles as capsules can be consistently achieved and thus PVA can surprisingly be used successfully in this novel application.

The capsule is most preferably sealed; this may prevent deterioration of the substance. The substance may be consumable. Particularly if the substance is consumable, the PVA composition may contain exclusively food grade ingredients. The PVA composition may contain a filler which is inert or consumable, for example calcium carbonate and/or a plant or vegetable derivative product, such as wood flour or rice husk.

The substance may be substantially solid, dry or powdered. The invention is particularly useful for facilitating provision of a sealed (one part, substantially unitary) capsule containing a solid substance. Hitherto, it has not been practicable to supply powdered substances encapsulated in sealed capsules on a large scale and the invention may surprisingly facilitate this.

The invention is particularly advantageous when applied to small capsules, for example having a volume of less than about 5 cm$^3$, more typically less than about 1 cm$^3$, often about 0.5 cm$^3$.

In a preferred embodiment, the invention provides a sealed capsule blow moulded from a PVA composition containing exclusively food grade ingredients and containing a consumable substance.

As noted above, most preferably the capsule is formed by blow moulding; this provides a surprisingly convenient means of reliably forming capsules. Historically, applications of PVA have been limited because of difficulties encountered in melt extruding it: namely, that melt extruded PVA becomes very unstable and significant residues become adhered to the extrusion apparatus; that very careful control of process conditions and specialised apparatus are required; and that the process has to be shut down and the apparatus purged frequently. Because of this unreliability, PVA has not generally been considered a suitable candidate for blow moulding in general as non-uniformities may lead to rupture of the film. In a relatively small and delicate capsule which may need to contain an accurately measured quantity of substance such problems would be even more severe. However, surprisingly, if the PVA has been compounded and cold-pressed as described herein it can be reliably melt-extruded into a blow-moulding apparatus, such as described herein, for forming capsules. These compositions may have similar mechanical properties to gelatin and may be edible, having an inoffensive taste. These compositions can thus successfully be used to substitute gelatin.

Apart from choice of a suitable material, there are several problems associated with blow moulding to a high standard of quality in a cost efficient manner. Extrusion blow moulding is a technique that is normally used for moulding hollow plastic articles such as bottles from thermoformable polymers. Conventionally the thermoformable polymer is first heat extruded into a preform or parison. Then a two part moulding die is closed around the preform. If the thermoformable polymer is too viscous for this to be feasible, the two part moulding die is first closed and the heat extruded thermoformable polymer is injected into it. Air is injected into the preform to expand the preform against the mould cavity. The preform is thus blow moulded into the shape of the cavity of the die. The mould is then opened/separated and the blow moulded article is removed. One of the problems is the minimisation of the cycle time to produce a moulded article. Embodiments of the present invention provide an apparatus including a mould arrangement that enables the blow moulding of a PVA composition to a reliable standard while minimising cycle time.

A second aspect of the present invention provides an apparatus for blow moulding a PVA composition into a capsule, the apparatus comprising means defining at least one moulding cavity, preferably a plurality of moulding cavities, means for injecting a PVA composition into each moulding cavity, preferably substantially simultaneously, means for inflating the PVA composition in each moulding cavity to form a capsule, means for filling each capsule with a substance and means for sealing each filled capsule.

The means defining a plurality of moulding cavities may comprise a mould made up of separable parts and preferably comprises a mould having two halves. If the mould comprises two halves, each mould half contains a series of respective recesses so that, when placed together, both halves form a mould comprising a row of cavities suitable for forming capsules. If the mould is made up of more than two separable parts, the parts should be such that, when placed in position together, they form a mould comprising a row of cavities suitable for forming capsules. Preferably the mould has at least about 10 cavities. The mould may have more, for example about 20 or about 30, cavities in a row. Typically the cavities will form capsules having a volume of less than 5 cm$^3$, more typically less than about 1 cm$^3$, often about 0.5 cm$^3$. Typically, the process involves bringing the mould parts (halves) together, injecting the heat extruded PVA composition into each mould, inflating the PVA composition in each mould to form a capsule, filling each capsule with a substance and sealing each filled capsule.

The use of the mould arrangement of the present invention i.e., the means defining a row of moulding cavities, enables the successive injection, inflation, filling and sealing of a number of capsules with just one act of placing of the mould parts (halves) together and one act of separation of the mould halves, thus minimising the number of times the mould parts (halves) have to be brought together and separated per formation of one filled capsule. Thus the cycle time to produce a moulded article is minimised. In the process of the present invention it is preferred that the step of filling is carried out so that the capsules are filled in quick succession. This may ensure consistent batches of capsules. For pharmaceutical applications in particular, the consistency and accuracy of the measured amount of filling is very important. Preferably the step of PVA injection is carried out for all of the cavities in quick succession, for example by moving the mould with respect to an injection source, or substantially simultaneously.

The apparatus may comprise physically separate stations for some or all of the steps of injection, inflation, filling and sealing. The apparatus may also comprise translation means for moving the mould form one station to another.

A suitable pressurised fluid, normally gas, may be used for inflating the PVA composition. Usually such means utilise compressed air. In a preferred embodiment of the present invention an inert gas such as nitrogen or argon is used to inflate the PVA composition. The capsule then contains a substantially inert atmosphere prior to filling with the substance. This has the advantage of minimising exposure of the substance to air. This is of particular importance for substances that are sensitive to air and/or that oxidise readily.

An injection nozzle may be used for filling the capsule. The capsule may be filled with a substance which may be in the form of a liquid or a powder. Previously gelatin capsules were generally used to contain only liquids and powdered medicaments were contained in two-part capsules. Therefore it is another surprising advantage of this invention that it produces a sealed, substantially one-part capsule that is suitable for containing powder. One-part capsules are more air tight than two-part capsules. One-part capsules are better for controlled-release applications as the thickness of the capsule walls is more even.

Although the capsules of the present invention are suitable for pharmaceutical applications, e.g. for containing pharmaceutical substances such as medicaments and suitable for containing dietary supplements such as vitamins, minerals and edible oils, they may also be used in other applications that require the (controlled) release of a substance by means of biodegrading or solubilising a capsule wall. An example of such another application is that of capsules containing bubble bath or bath oil. A further example is a capsule containing a detergent powder or liquid, for example for use in a dishwasher or washing machine. Such capsules may have a larger capacity, for example up to 10 cubic centimetres or even larger. A detergent dispenser, for example for a dishwasher or washing machine, comprising a quantity of detergent (liquid or powdered) in a soluble capsule formed from a PVA composition, preferably a cold-water soluble composition (optionally a warm or hot water soluble composition) may be provided independently according to a further aspect of the invention.

Preferably the sealing is done by means of a knife. Preferably the knife is heated and is passed over the top of the capsule thereby sealing the top of it. The mould arrangement is such that more than one capsule can be sealed by the same passing stroke of the knife. This is therefore a particularly fast, clean and efficient way of sealing the capsules. This sealing method helps minimise the exposure of the substance contained in the capsule to air. This is particularly important for substances which are sensitive to air and/or oxidise easily. The mould parts (halves) are then separated and the filled capsules released.

Further aspects and preferred features are set out in the claims.

An embodiment of the invention will now be described, by way of example only, with reference to the accompanying drawings in which.

In the figures, like parts are designated by like reference numerals.

Figure 1:
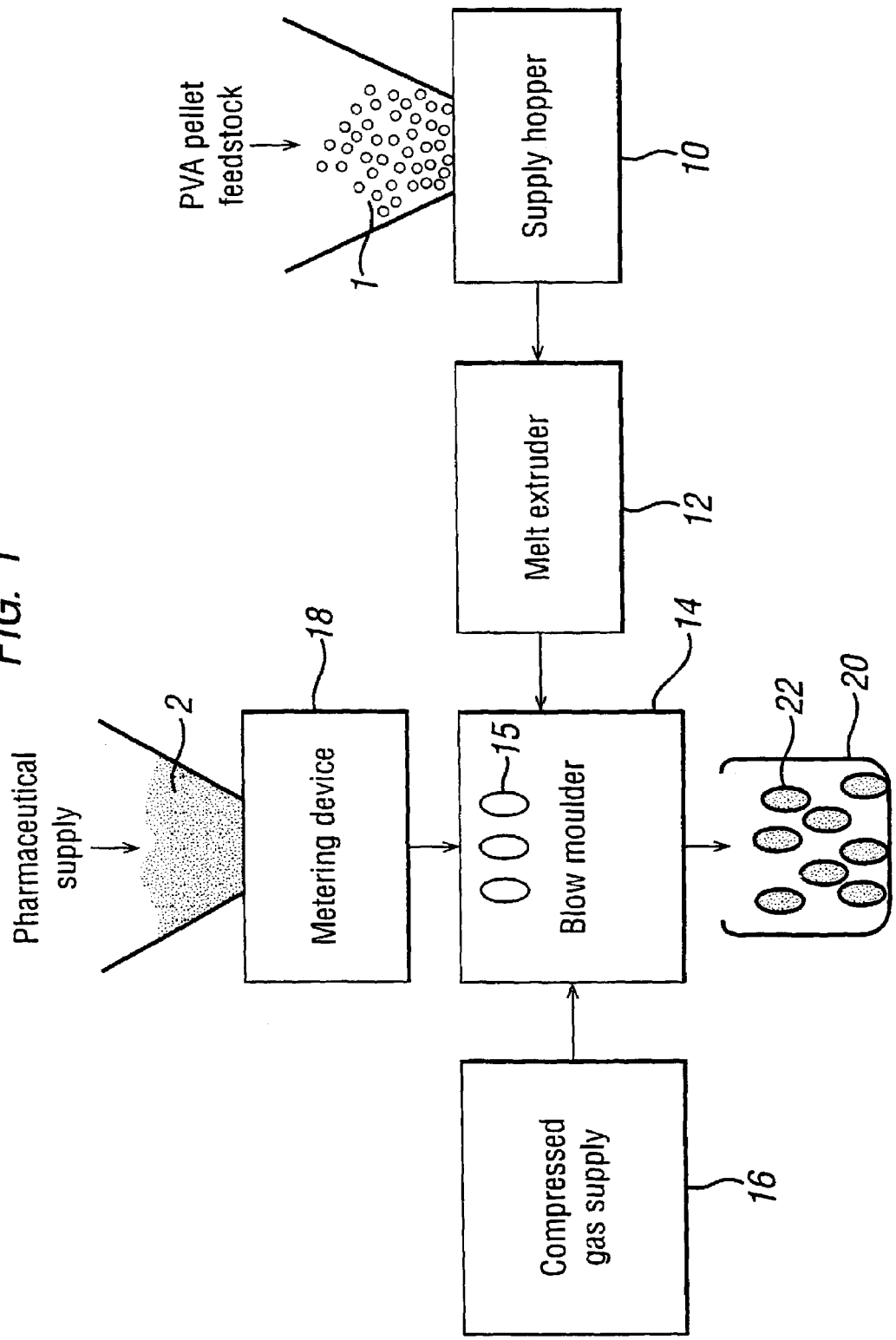
FIG. 1 is a generalised schematic diagram of apparatus according to an embodiment of the invention

Referring to FIG. 1, a supply of PVA pellet feedstock 1 is provided via a supply hopper 10 (or other suitable feeding arrangement) to a melt extruder 12 which may comprise a screw type extruder as typically used to extrude conventional thermoplastics, the output of which is supplied to blow moulder 14. The blow moulder has a plurality of moulding cavities 15, to be described further below, in which capsules are formed and receives a supply of compressed gas 16 and a supply of a substance to be encapsulated 2 via a metering device 18. In the embodiment shown, the substance is a pharmaceutical but other substances may be used, for example detergents. Although the apparatus is shown as separate parts, the functions may be integrated, in particular the function of the metering apparatus is conveniently integrated into the portion of the blow moulder which fills the capsules. The blow moulder ejects filled capsules 22 into a suitable container 20.

Figure 2:
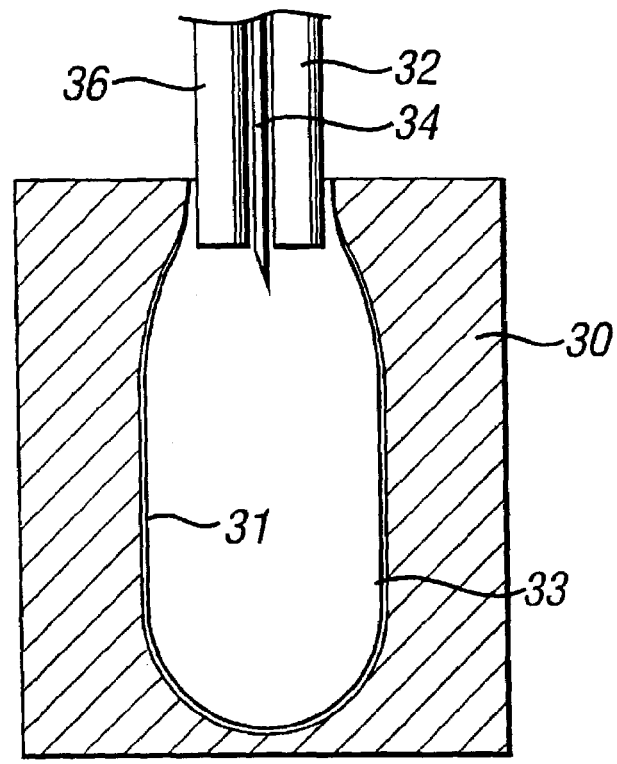
FIG. 2 shows a schematic front view of a capsule forming cavity.
Figure 3:
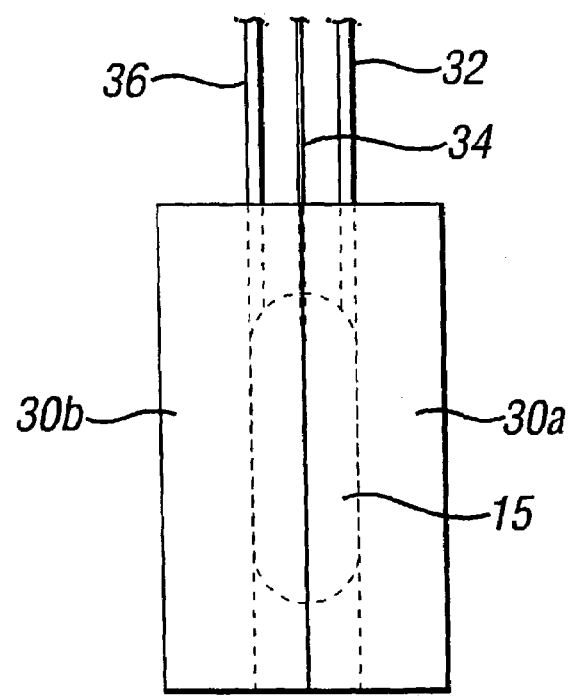
FIG. 3 shows schematic side view of a capsule forming cavity showing the opposed mould halves.

Referring to FIGS. 2 and 3, a mould 30 formed from opposed mould halves 30a, 30b provides a plurality of cavities in the shape of the capsule desired. A single ellipsoidal cavity 15 is shown in FIG. 2. A more complex shape may be formed and this may incorporate a logo, for example. A thin wall of PVA composition 31 is formed within the mould cavity from an injected stream 36 of PVA derived from melt extruder 12. Whilst in some cases the polymer may be directly injected into the cavity, more preferably a preformed section of polymer, typically tubular, is extruded and this section is trapped between opposed mould halves, closure of the mould halves sealing an end. The capsule is inflated by means of compressed gas injected through nozzle 32 opposite the trapped end so that it fills the cavity and liquid or powdered substance to fill the capsule may be injected by means of needle 34. The needle must be of sufficient bore to permit liquid to flow under the conditions of liquid viscosity and pressure expected. Similarly, for powdered substances, the bore must be sufficient to avoid clogging. Such considerations are well known to those skilled in the art of filling medicament capsules and it will be appreciated that problems may be alleviated by enlarging the injection orifice or increasing injection pressures, or by reducing particle size or viscosity, for example by processing solids or by adding diluents to liquids.

After injection of the substance, the needle is withdrawn and the capsule is preferably sealed. If the polymer is sufficiently molten and the needle sufficiently small, the capsule may self seal. More preferably, to ensure reliable sealing, a heated knife or other implement is drawn across the capsule in the region of the needle opening to cause local melting and sealing of the capsule. Excess not cut off directly by the action of the mould halves coming together or by the sealing knife may be trimmed, although normally a seam will remain. A visible seam can provide an assurance that the capsule integrity remains and this may be useful in the case of a pharmaceutical or consumable capsule and may be provided for decorative or advertising purposes in other cases. The invention independently provides a sealed capsule, particularly a pharmaceutical, formed from PVA containing a substance and having a seam.

Figure 4:
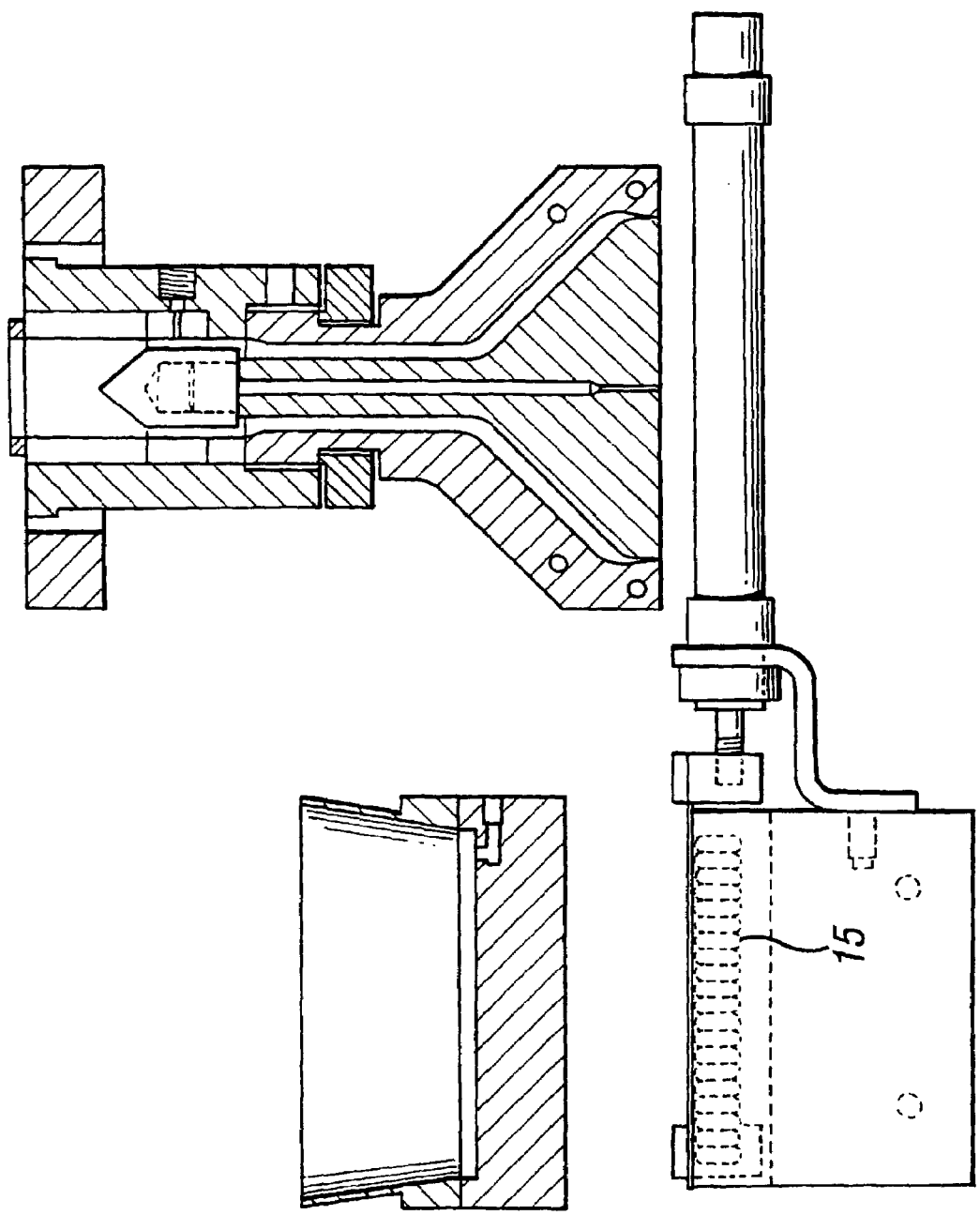
FIG. 4 shows a front view of blow moulding apparatus having a plurality of moulding cavities.
Figure 5:
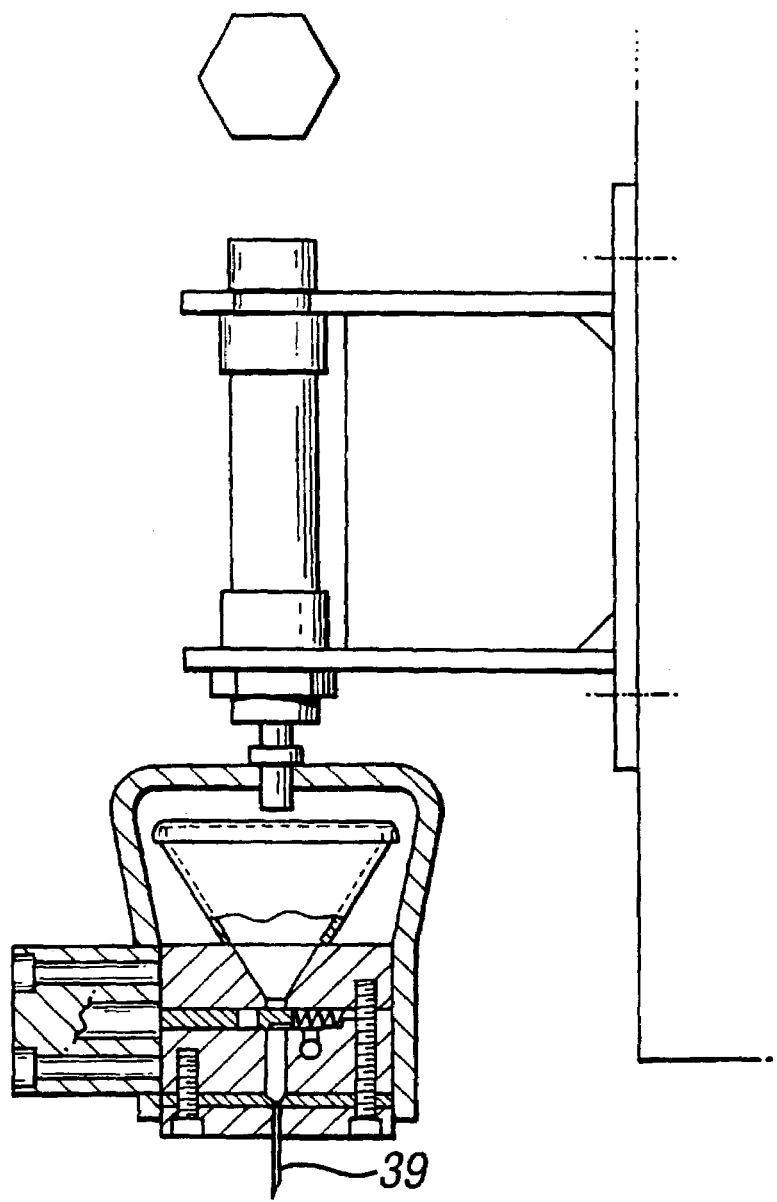
FIG. 5 shows a section through the apparatus of FIG. 4.
Figure 5:
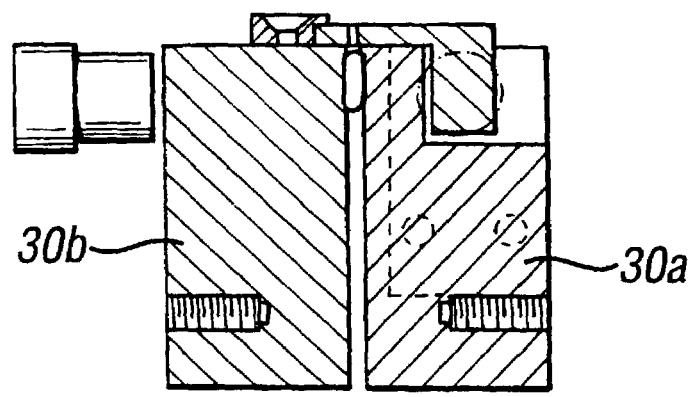

FIGS. 4 and 5 show an example of a practical mould embodying the principles shown in the schematic figures. This example shows a single needle assembly 39 used for injecting polymer, air and substance. A row of needle assemblies can be used to fill a row of capsules simultaneously or a single needle assembly, or smaller number of needle assemblies may be used to fill a proportion only of the cavities and translated relative to the mould to complete the process of filling all cavities. The substance may be injected by means of a needle separate from the assembly that supplies the polymer. Not shown, the mould is preferably provided with cooling to ensure more rapid solidification of the injected polymer. Multiple rows of multiple capsules may be supplied from a single extruder; as will be appreciated, the greater the number of mould cavities, the greater the rate of capsule production that can be achieved. The invention can be applied to a mould having a single cavity. However, whilst not excluded, this is less preferred for capsule formation due to the larger cycle time required; a particular advantage is provided by the use of a mould defining a plurality of cavities.

The PVA-containing composition used to form the feedstock 1 in the embodiments is in the form of cold-pressed pellets or tablets and preferably comprises a blend of PVA and an amount of lubricant effective to render the blend extrudable. The lubricant preferably comprises a fatty acid amide or a plasticiser or a mixture of both a fatty acid and a plasticiser, the resultant blend being suitable for extrusion in conventional melt-extrusion apparatus. The composition typically has a flexural modulus similar to other extrudable polymers. Known advantageous properties of PVA, such as high tensile strength, good puncture resistance and good barrier characteristics are retained in this composition.

Preferred feedstock comprises a PVA-containing composition comprises up to 20%, especially 5 to 15%, plasticizer and up to 5%, especially 0.5 to 2.5%, lubricant, by weight.

In embodiments of the invention, extrudable and blow mouldable PVA-containing compositions have been obtained comprising fully hydrolysed PVA as well as partially hydrolysed PVA, and including PVA that is 70% or more hydrolysed.

The PVA-containing compositions may have a molecular weight of the PVA varying from around 20,000, in some cases from around 10,000, to greater than 150,000. Generally, the application of the present invention is not limited to PVA of any particular percent hydrolysis nor of any particular molecular weight.

The lubricant composition of the invention is provided so as to improve the thermal instability of the composition under extrusion. The lubricant may be referred to as an internal lubricant, in that its function is to improve lubrication between the polymer chains.

Compositions of the invention may be intended for consumption and hence it is preferred that the lubricant is approved for this purpose. It is further preferred that the lubricant is a fatty acid amide, and particularly a straight or branched $C_{12}$–$C_{24}$ fatty acid amide, more particularly $C_{16}$–$C_{20}$. Particularly and surprisingly good results are obtained if the lubricant comprises stearamide, a straight chain $C_{18}$ fatty acid amide.

The compositions of the invention typically further include a plasticiser, to lower the melt temperature of the polymer under extrusion. The plasticiser may suitably be selected from glycerine, ethylene glycol, triethylene glycol, low molecular weight polyethylene glycols and low molecular weight amides. A particularly preferred plasticiser comprises or consists of glycerol.

While the proportion of components present may vary in compositions of the invention, embodiments of the invention generally comprises, by weight, up to 50% filler and up to 5% lubricant. More particular embodiments of the invention comprise, by weight, 5–50% filler, 40–80% PVA, up to 5% lubricant and 5–20% plasticiser.

Good results have been obtained with embodiments having the following make up, by weight:
(a) 40 to 80% PVA;
(b) 5 to 50% filler;
(c) 5 to 15% plasticiser, preferably glycerol;
(d) 0.5 to 2.5% lubricant, preferably a fatty acid amide as an internal lubricant, most preferably octodecanamide.

Particularly good results have been obtained in embodiments of the invention having the following make up, by weight:
(a) 40 to 70% PVA;
(b) 20 to 50% filler, preferably a micronised inorganic material such as talc, preferably coated with stearate;
(c) 8 to 15% plasticiser, preferably glycerol;
(d) 0.5 to 1.5% internal lubricant, preferably a fatty acid amide, most preferably octodecanamide; and
(e) 0.0001 to 0.1% external lubricant, preferably stearate.

The composition may contain residual moisture, sufficient to enable the composition to be bound as a cold-pressed tablet.

Exemplary compositions which may be employed for the feedstock will now be detailed.

EXAMPLE 1

A blend of, by weight, approximately 60% fully hydrolysed PVA, 30% calcium carbonate, 10% glycerol, 0.01% zinc stearate and 1% octodecanamide was prepared in a high speed blender. It was found to have a white/cream colour with the following properties:

| | |
|---|---|
| density | 1.65 g/cm³ |
| melt density | 1.46 g/cm³ at 200° C. (under ISO 1183) |
| MFR | 357 (10 mins/200° C./21.6 kilograms, under ISO 1133) |
| melt temperature | 200° C. |
| processing temperature | 190–200° C. |
| residence time | up to 15 minutes |
| drying time | 4 hours at 80° C. |

EXAMPLE 2

A blend was prepared in a similar way to example 1 of, by weight, approximately 60% partially hydrolysed PVA, 30% calcium carbonate, 10% glycerol, 0.01% zinc stearate and 1% octadecanamide. This was found to have the following properties:

| | |
|---|---|
| density | 1.65 g/cm³ |
| melt density | 1.38–1.40 g/cm³ at 190° C. (under ISO 1183) |
| MFR | 22 (10 mins/190° C./5 kilograms, under ISO 1133) |
| apparent melt viscosity | 236/49 (Pa.s 1,000 s/10,000 s) |
| melt temperature | 200° C. |
| processing temperature | 190–200° C. |
| residence time | up to 15 minutes |
| drying time | 4 hours at 80° C. |

The compositions of both examples 1 and 2 were satisfactorily extruded and blow moulded.

EXAMPLE 3

The PVA-containing compositions of examples 1 and 2 were examined for their extrudability in injection-moulding machines made by Brabender, Killion, Windsor, Hesas, Battenfield, Fischer, Demag and Arburg. Extrusion processing was carried out using a single full flight screw with constant pitch. The barrel temperature had a profile of 180–200° C. (melt 190–210° C.) and the screw speed varied typically between 20 and 120 rpm. Shut down of the apparatus was carried out by maintaining the temperature for up to 15 minutes with screw rotation stopped, over a period of 3 hours reducing the temperature to 100° C. with screw rotation stopped and subsequently completing the shut down by turning the machine off.

Whether or not a given composition is extrudable (by which is meant on commonplace extrusion apparatus) will normally be clear to one skilled in the art. In the event that a test is required, however, it is suggested that extrudability is determined by attempting extrusion on one or more of the above-named manufacturers machines using a single full flight screw with constant pitch with speeds and temperatures in the above range. If the composition extrudes reliably on at least two of the above machines with routine adjustment of parameters, it is to be deemed extrudable; if consistent problems are obtained and extrusion is only possible under highly specific conditions or on specialised equipment, it is to be deemed not to be extrudable.

EXAMPLES 4–9

PVA-containing compositions were prepared as blends of the following components in the amounts shown:

| | EXAMPLE | | | | | |
|---|---|---|---|---|---|---|
| Components | 4 | 5 | 6 | 7 | 8 | 9 |
| PVA - fully hydrolysed | — | — | — | 50 | 60 | 55 |
| PVA - partially hydrolysed | 50 | 60 | 55 | — | — | — |
| Calcium carbonate (coated) | 40 | 30 | 30 | 40 | 30 | 30 |
| Glycerol | 9 | 9 | 14 | 9 | 9 | 14 |
| Octadecanamide | 1 | 1 | 1 | 1 | 1 | 1 |
| Zinc Stearate | 0.01 | 0.01 | 0.01 | 0.01 | 0.01 | 0.01 |

As far as extrusion apparatus is concerned, it is advantageous to use chrome plated screws and for the melt flow path to use chrome plated surfaces and gradual tapers to streamline the melt.

As an alternative to calcium stearate as a filler, organic substances such as rice husk and wood flour may be used.

Embodiments of the invention thus provide capsules formed from PVA-containing compositions which are biodegradable.

Aspects of the invention may further provide independently or in combination any one or more of the preferred or optional features disclosed herein and/or any one or more of (I) use of a PVA composition in the manufacture of a capsule (ii) a sealed blow-moulded PVA capsule containing a powdered substance (iii) a pharmaceutical composition contained within a PVA capsule (iv) a method of sealing a blow moulded PVA capsule containing a substance comprising melting a portion of the capsule and (v) use of PVA in the manufacture of a consumable capsule containing a medicament for the treatment of a condition in a patient averse to consumption of gelatin. In preferred applications, particularly pharmaceuticals and food supplements, the PVA composition is preferably cold-water soluble. In detergent dispenser applications, the solubility temperature may be selected to provide controlled or delayed release. In certain applications, for example paintball capsules, hot water soluble PVA may be used. The appended abstract is incorporated herein by reference. Reference numerals appearing in the claims shall have no limiting effect.

The invention claimed is:

1. An injection blow-moulded capsule having walls formed from a polyvinyl alcohol (PVA) containing composition, the walls enveloping a consumable substance, wherein the PVA composition consists essentially of 40%–80% by weight partially hydrolyzed PVA, 5 to 15% by weight of a plasticizer, 0.5% to 2.5% by weight a straight or branched chain $C_{12}$ to $C_{24}$ fatty acid amide as a lubricant and 5 to 50% of an inert or consumable filler comprising calcium carbonate.

2. A capsule according to claim 1 wherein the PVA comprises partially hydrolysed PVA having a molecular weight of at least about 10,000.

3. A capsule according to claim 1 wherein the plasticizer comprises glycerol.

4. A capsule according to claim 1 wherein the fatty acid amide comprises a $C_{16}$ to $C_{20}$ fatty acid amide.

5. A capsule according to claim 4 wherein the fatty acid amide comprises stearamide.

6. A capsule having walls formed from a polyvinyl alcohol (PVA) containing composition and containing a consumable substance, wherein the PVA composition consists essentially of 40–80% by weight partially hydrolyzed PVA, 5 to 10% by weight plasticizer, 0.5% to 2.5% of a straight or branched chain $C_{12}$ to $C_{24}$ fatty acid amide as a lubricant, 5 to 50% of an inert or consumable filler comprising calcium carbonate, and stearate as an external lubricant.

7. A capsule according to claim 1 wherein the capsule is sealed.

8. A capsule according to claim 1 wherein the substance is consumable and, wherein the PVA composition contains exclusively food grade ingredients.

9. A capsule according to claim 1 wherein the capsule has a volume of 5 cubic centimeters or less.

10. A capsule according to claim 1 wherein the capsule contains a measured dose of a pharmaceutical substance.

* * * * *